(12) United States Patent
Kawabata et al.

(10) Patent No.: US 9,741,627 B2
(45) Date of Patent: Aug. 22, 2017

(54) SUBSTRATE ETCHING APPARATUS AND SUBSTRATE ANALYSIS METHOD

(71) Applicant: IAS Inc., Tokyo (JP)

(72) Inventors: Katsuhiko Kawabata, Tokyo (JP); Takuma Hayashi, Tokyo (JP); Mitsumasa Ikeuchi, Tokyo (JP); Sungjae Lee, Tokyo (JP); Jin Kunika, Tokyo (JP)

(73) Assignee: IAS, INC, Tokyo (JP)

( * ) Notice: Subject to any disclaimer, the term of this patent is extended or adjusted under 35 U.S.C. 154(b) by 37 days.

(21) Appl. No.: 14/766,981

(22) PCT Filed: Jan. 21, 2014

(86) PCT No.: PCT/JP2014/051032
§ 371 (c)(1),
(2) Date: Aug. 10, 2015

(87) PCT Pub. No.: WO2014/129246
PCT Pub. Date: Aug. 28, 2014

(65) Prior Publication Data
US 2015/0357249 A1    Dec. 10, 2015

(30) Foreign Application Priority Data
Feb. 21, 2013    (JP) .............................. P2013-032433

(51) Int. Cl.
*C23F 1/00*    (2006.01)
*H01L 21/306*    (2006.01)
(Continued)

(52) U.S. Cl.
CPC ........ *H01L 22/12* (2013.01); *H01J 37/32449* (2013.01); *H01J 37/32834* (2013.01);
(Continued)

(58) Field of Classification Search
CPC .............. H01L 22/12; H01L 21/67069; H01L 21/3065; H01J 37/32449; H01J 37/32834;
(Continued)

(56) References Cited

U.S. PATENT DOCUMENTS

| | | |
|---|---|---|
| 6,230,722 B1 | 5/2001 | Mitsumori et al. |
| 2001/0037819 A1 | 11/2001 | Mitsumori et al. |

(Continued)

FOREIGN PATENT DOCUMENTS

| | | |
|---|---|---|
| JP | 11-33506 A | 2/1999 |
| JP | 2004-339566 A | 12/2004 |

(Continued)

*Primary Examiner* — Julio J Maldonado
*Assistant Examiner* — Stanetta Isaac
(74) *Attorney, Agent, or Firm* — Roberts & Roberts, LLP

(57) ABSTRACT

The present invention provides an etching apparatus suitable for etching polysilicon on a substrate or bulk silicon constituting the substrate. The present invention relates to an etching apparatus including a gas-flow adjusting means that allows etching gas to flow from a periphery of a substrate to substantially a center of the substrate, and relates to a technology capable of etching polysilicon or bulk silicon at a uniform thickness on an entire substrate surface. In addition, the gas-flow adjusting means is installed in a vertically movable manner, and an etching speed can be controlled by an adjustment of the gas-flow adjusting means.

20 Claims, 2 Drawing Sheets

(51) Int. Cl.
*H01L 21/66* (2006.01)
*H01L 21/67* (2006.01)
*H01J 37/32* (2006.01)
H01L 21/3065 (2006.01)
G01N 1/32 (2006.01)

(52) U.S. Cl.
CPC .......... *H01L 21/67069* (2013.01); *G01N 1/32* (2013.01); *H01J 2237/334* (2013.01); *H01L 21/3065* (2013.01)

(58) Field of Classification Search
CPC ........ H01J 2237/334; G01N 1/32; C23F 1/08; H05K 3/068; B24B 37/005; B24B 37/015; B24B 49/00; B24B 49/04
USPC .............. 156/345.1, 345.13, 345.15, 345.26, 156/345.29; 216/8, 9, 10
See application file for complete search history.

(56) References Cited

U.S. PATENT DOCUMENTS

2007/0281106 A1* 12/2007 Lubomirsky ......... C23C 16/401
  427/569
2008/0003792 A1* 1/2008 Chae ................. H01L 21/02071
  438/592

FOREIGN PATENT DOCUMENTS

JP    2005-265718 A    9/2005
JP    2011-95016 A     5/2011

\* cited by examiner

SUBSTRATE ETCHING APPARATUS AND SUBSTRATE ANALYSIS METHOD

TECHNICAL FIELD

The present invention relates to an apparatus used for etching in substrate analysis, and more particularly to an apparatus suitable for etching polysilicon formed on a substrate or bulk silicon serving as a constitutional material of a substrate.

BACKGROUND ART

A substrate such as a semiconductor wafer on which a silicon oxide film, a nitride film, or the like is formed as a configuration of the substrate using a base material composed of silicon or the like is known. A contaminant such as metal or an organic material may contaminate the material constituting the semiconductor substrate in a manufacturing process, and even a small amount of the contaminant significantly lowers semiconductor characteristics. For this reason, there is a demand for a technology of analyzing a small amount of a contamination source included in the substrate as an analysis object.

In the analysis of a small amount of the contamination source included in the substrate, for example, there is known a method of decomposing a constitutional film of a substrate by etching, ejecting an analysis recovery liquid onto the substrate after etching, moving the recovery liquid on the substrate, shifting the analysis object into the liquid, collecting the analysis object, and analyzing the recovery liquid qualitatively and quantitatively by inductively coupled plasma (ICP) analysis or the like.

A vapor-phase decomposition method using etching gas generated by bubbling a mixed acid solution formed of nitric acid or hydrogen peroxide mixed with a hydrofluoric acid or the like is known as etching of a constitutional film of a substrate, and an apparatus that includes a chamber in which a substrate is arranged and that is capable of introducing etching gas into the chamber is used as an etching apparatus for the above-described method. For example, as disclosed in Patent Document 1, etching gas can be supplied from an etching gas introduction port provided in a chamber (FIG. 1 in Patent Document 1). The etching gas arbitrarily flows to the space in the chamber, and only gas contacted a substrate surface among the flown etching gas contributes to etching of the substrate. In this way, a flow direction of the etching gas is not particularly controlled in the chamber, but since etching gas having a relative low etching performance such as a mixed acid solution of hydrofluoric acid is used as the etching gas, it is possible to etch only a formed film of interest such as an oxide film or a nitride film.

Here, in the substrate analysis, as a formed film of which contamination source needs to be analyzed, it is also necessary to analyze a formed film relatively difficult to decompose such as polysilicon or a substrate itself (bulk silicon) in addition to a formed film relatively easy to decompose such as the above-described oxide film or nitride film. In such analysis of the polysilicon or the substrate itself, etching gas having a high etching performance is necessary, and, for example, a technology using a solution formed of ozone water added to a mixed acid solution (Patent Document 2) and a technology using vapor of hydrogen fluoride and ozone-containing gas (Patent Document 1) have been proposed.

RELATED ART DOCUMENT

Patent Documents

Patent Document 1: JP 2011-95016 A
Patent Document 2: JP 2005-265718 A

SUMMARY OF THE INVENTION

Problems to be Solved by the Invention

When the polysilicon or the substrate itself is analyzed, since gas having a high etching performance such as the above-described etching gas containing ozone is used, it has been difficult for the conventional etching apparatus to uniformly progress etching in a depth direction of the entire surface of the substrate. For example, when the conventional etching apparatus etches the polysilicon or the bulk silicon itself serving as the substrate with etching gas containing ozone, an etching depth measured after etching has a variation of about −40% to +100% in the thickness direction of the substrate from a target etching depth, and etching becomes non-uniform.

In substrate analysis of a semiconductor substrate or the like, since it may be necessary to specify the position of a contaminant even in the thickness direction of the substrate, a technology capable of performing uniform etching in the thickness direction of the substrate becomes necessary. In addition, when the etching in the thickness direction of the bulk silicon serving as the substrate becomes non-uniform, an adverse effect is also likely to occur, for example, when semiconductor substrate characteristics and the like are evaluated. In addition, in order to cope with an increase in the diameter of the substrate, a technology capable of etching the entire substrate surface uniformly in the surface direction of the substrate is needed for large-area substrates.

Therefore, the present invention provides an etching apparatus capable of etching uniformly in the thickness direction of a substrate such as semiconductor substrates while etching uniformly an entire surface of the substrate. Particularly, the present invention provides an etching apparatus also capable of etching uniformly polysilicon serving as a formed film of the substrate and bulk silicon of the substrate itself.

Means for Solving the Problems

The present invention to solve the above problems relates to an etching apparatus including a chamber in which a substrate is arranged on a bottom portion, the etching apparatus including: a gas supply means that supplies etching gas to a substrate surface; a gas exhaust means that exhausts gas after etching above substantially a center of the substrate; and a gas-flow adjusting means that is arranged on a substantially concentric circle above the substrate and allows the etching gas to flow in a direction from a periphery of the substrate to substantially the center of the substrate, wherein the gas-flow adjusting means is installed to be vertically movable, and substantially a center of the gas-flow adjusting means is connected with the gas exhaust means.

With the etching apparatus of the present invention, it is possible to uniformly progress etching by controlling the flow direction of the etching gas in the chamber by the gas-flow adjusting means, and particularly, it is possible to reduce a variation in the thickness direction of the substrate. Specifically, since the flow of the etching gas in the chamber is controlled by the gas-flow adjusting means to be only a flow in a constant direction from the periphery of the substrate to the center of the substrate, a contact between the substrate and the etching gas progresses sequentially from the periphery of the substrate to the center of the substrate and contributes to uniform etching.

Here, the etching performance of the substrate with the etching gas is known to generally lower with the progress of the etching process. This is because a component in the etching gas contributing to the etching is consumed and reduces with the progress of the etching. Thus, when the etching gas contacts the substrate in the first half of the etching process, the etching of the substrate easily progresses, and when the etching gas contacts the substrate in the second half of the etching process, the etching tends to be difficult to progress. This has been a factor causing a variation depending on an etching position in the surface direction of the substrate.

In contrast, the present invention realizes uniform etching on the entire surface of the substrate even in the surface direction of the substrate, by controlling the flow direction of the etching gas to be a direction from the periphery of the substrate to the center of the substrate. Specifically, in the present invention, the etching gas supplied to the periphery of the substrate by the gas supply means is exhausted above substantially the center of the substrate by the gas exhaust means to control flow direction of the above-described gas to be the direction from the periphery of the substrate to the center of the substrate. In this way, allowing the gas to flow from the periphery of the substrate to the center of the substrate makes it possible to gradually reduce the etching target area of the substrate from the peripheral portion having a larger diameter to the central portion having a smaller diameter. Thus, since the etching area is gradually reduced with the progress of the etching process, there is little influence of consumption and reduction of the etching component, and an etching variation in the surface direction of the substrate can be suppressed.

Hereinafter, the respective configurations of the etching apparatus of the present invention will be described in detail.

The gas supply means introduces the etching gas into the chamber, and can be installed at an arbitrary position of the chamber. However, but in view of the gas flow control by the present apparatus, the gas supply means is preferably installed on an upper surface portion of the chamber or an upper side of a side surface of the chamber. More preferably, the gas supply means is installed on the upper surface of the chamber. This is because the etching gas easily diffuses uniformly via the gas-flow adjusting means to the substrate arranged on the bottom portion of the chamber.

Then, the gas-flow adjusting means is arranged on a substantially concentric circle above the substrate so as to introduce the etching gas into the space between the gas-flow adjusting means and the substrate. Accordingly, it is possible to introduce the etching gas introduced into the chamber by the gas supply means into the space between the gas-flow adjusting means and the substrate surface and control the flow of the etching gas from the periphery of the substrate to substantially the center of the substrate. In addition, the gas-flow adjusting means has a function of blocking the etching gas from being introduced to the substrate surface from the inner circumferential side other than the periphery of the substrate. That is, the etching gas introduced from the upper layer side of the chamber is guided to peripheral side of the substrate by the gas-flow adjusting means and introduced to the substrate surface only from the outer circumferential side of the gas-flow adjusting means without flowing directly to the inner circumference or the like of the substrate.

The shape of the gas-flow adjusting means can be an arbitrary shape, and is not particularly limited. For example, preferably, the gas-flow adjusting means has a disk shape or a substantially conical shape having an apex on a substrate side. As the size (maximum diameter) of the gas-flow adjusting means, almost the same size as the diameter of the substrate can be applied. When the size of the wafer is too larger than that of the gas-flow adjusting means, the etching rate easily varies in the outer circumference and at the center of the wafer. A suitable range of the maximum diameter of the gas-flow adjusting means differs according to the size of the substrate serving as the etching target, but for example, when the wafer of 150 to 450 mm is etched, the diameter ($D_{gas}$) of the gas-flow adjusting means suitably ranges from 0.3 to 1.5, more suitably from 0.5 to 1.1 as a value ($D_{gas}/D_{wafer}$) to the diameter ($D_{wafer}$) of the substrate.

When the gas-flow adjusting means has a disk shape, the number of disks may be one or more. In addition, the gas-flow adjusting means of the conical shape and the gas-flow adjusting means of the disk shape may be combined and installed. When a plurality of disks is included, the respective disks can have different diameters. Particularly, the disks are preferably arranged in a multi-stage manner such that that the diameter is increased sequentially from the upper portion to the bottom portion of the chamber. This is because the etching gas easily flows from the outer circumferential sides of the gas-flow adjusting means to the substrate surface from the upper portion of the chamber.

In addition, when the gas-flow adjusting means has the disk shape, it is preferable that the means be processed such that the thickness near the outer circumference decreases as it gets closer to the outer circumferential end side, and have a notch-like portion. In the gas-flow adjusting means, the notch portion may be provided on any of the lower side facing the substrate and the upper side opposite to the substrate side, but is preferably provided on the lower side facing the substrate. When the notch portion is provided, the etching gas smoothly flows from the outer circumference of the gas-flow adjusting means to the substrate surface, and for example, a turbulent flow of the etching gas flowing to portions other than the substrate surface such as a counter flow flowing to the upper portion of the chamber can be suppressed.

The gas-flow adjusting means is installed to be movable vertically. Changing the vertical position of the gas-flow adjusting means makes it possible to adjust the flow speed of the etching gas introduced between the gas-flow adjusting means and the substrate and control the etching rate. For this reason, it is preferable to change the vertical position of the gas-flow adjusting means in view of the supply amount or the exhaust amount of the etching gas, the diameter of the substrate, and the like. This is because more uniform etching can be performed.

In addition, the etching apparatus of the present invention includes a gas exhaust means that exhausts gas after etching above substantially the center of the substrate. The gas exhaust means is connected with substantially the center of the gas-flow adjusting means, and this exhaust flow induces the etching gas flow from the periphery of the substrate to substantially the center of the substrate.

A suitable example of the etching apparatus of the present invention described above includes the following apparatus. That is, preferably, in the apparatus of the present invention, an upper portion of the chamber is closed by a lid, an exhaust pipe serving as the gas exhaust means is inserted into a through hole formed at a center of the lid, a leading end of the exhaust pipe is arranged above substantially the center of the substrate, a gas introduction section through which the etching gas is introduced into the chamber is included between an inner circumference of the through hole of the lid and an outer circumference of the exhaust pipe, and the etching gas is introduced through the gas introduction section, flows from the outer circumference of the gas-flow adjusting means to the substrate surface, and is exhausted from the leading end of the exhaust pipe.

In such an apparatus, as the gas supply means, a gas introduction section through which the etching gas is introduced into the chamber is installed between the inner circumference of the through hole of the lid and the outer circumference of the exhaust pipe. In addition, the exhaust pipe is installed as the gas exhaust means. The flow of the etching gas when this apparatus is used will be described. The etching gas is introduced through the gas introduction port, flows toward the gas-flow adjusting means arranged above the substrate, and does not flow directly to the substrate surface. Then, the etching gas blocked by the gas-flow adjusting means spreads and flows in the outer circumferential direction of the gas-flow adjusting means, and when the etching gas flows up to the outer circumference, the etching gas is introduced from the peripheral side of the substrate to the substrate surface. Then, since the leading end of the exhaust pipe is arranged above near the center of the substrate, the etching gas flows from the outer circumferential portion (periphery) to the center of the substrate due to the exhaust force of the exhaust pipe. Such flow control of the etching gas enables uniform etching of the substrate.

In the etching apparatus of the present invention, it is preferable to provide a buffer chamber that uniformly mixes the etching gas to be introduced into the chamber. The buffer chamber is preferably installed on the upper portion of the lid. Uniformizing the concentration and composition of the etching gas to be introduced into the chamber makes it easy to realize a uniform etching process. For example, when the mixture of the vapor of the hydrogen fluoride and the ozone-containing gas is used as the etching gas, the mixed state of the hydrogen fluoride and the ozone in the etching gas is uniformized in the buffer chamber, and the etching gas having uniform composition and concentration is introduced into the chamber. Accordingly, a more uniform etching process can be realized.

An analysis apparatus such as an inductively coupled plasma (ICP) apparatus may be prepared as a separate apparatus, and an apparatus that performs only etching may be used as the etching apparatus of the present invention. However, an apparatus capable of introducing a sample after etching directly into the analysis apparatus such as the ICP apparatus and performing simultaneous analysis may be used.

As a method of analyzing a substrate by using the etching apparatus of the present invention described above, a method of etching polysilicon on the substrate or bulk silicon of the substrate with ozone-containing etching gas is suitable.

According to the etching apparatus of the present invention, even when the polysilicon on the substrate or the bulk silicon of the substrate is etched with ozone-containing etching gas having a high etching performance, it becomes possible to perform uniform etching in the thickness direction of the substrate.

As the ozone-containing etching gas, gas that contains both vapor of hydrogen fluoride and ozone can be applied. The ozone in the etching gas can be generated by discharging oxygen-containing gas. As the oxygen-containing gas, a mixture of oxygen, nitrogen, and/or argon can be used (hereinafter, the etching gas containing the ozone may be referred to simply as "ozone-containing gas"). In the present invention, as the etching gas, gas in which the ozone-containing gas generated by discharging is used as an ozone source, and a hydrofluoric acid solution or the like is separately used as a crude material and mixed with vapor of hydrogen fluoride generated by bubbling or the like is particularly suitable.

In the above-described analysis method, preferably, a ratio (H/D) of a distance (H) in the height direction between the substrate surface and the lowest end of the gas-flow adjusting means to a diameter (D) of the substrate is 1/60 to 1/10. As described above the vertical position of the gas-flow adjusting means has influence on the flow speed of the etching gas. When H/D is less than 1/60, the space between the gas-flow adjusting means and the substrate is narrow, and the etching gas is difficult to flow, and thus it is difficult to progress uniform etching. On the other hand, when H/D exceeds 1/10, the space between the gas-flow adjusting means and the substrate is large, and it becomes difficult to control the flow of the etching gas from the periphery of the substrate to the center of the substrate, and thus a turbulent flow in a different direction easily occurs.

In addition, in the etching method of the present invention, it is preferable to appropriately adjust the temperature of the substrate. When the temperature of the substrate is too low, the etching gas is condensed, and non-uniform etching easily progresses. On the other hand, when the temperature of the substrate is too high or the temperature of the substrate is increased by an etching reaction, it becomes difficult for the etching gas to contact the surface of the substrate, and the etching time tends to be long. For this reason, it is preferable to adjust the temperature of the substrate in view of the composition of the etching gas, the supply amount or the exhaust amount of the etching gas, and the like. For example, when the etching gas is supplied at 2 L/min, and is exhausted at 2 L/min, the temperature of the substrate is preferably 15° C. to 25° C., particularly preferably 18° C. to 23° C.

Advantageous Effects of the Invention

As described above, according to the etching method of the present invention, a uniform etching process even in a thickness direction of a substrate such as a semiconductor substrate can be realized. Particularly, even when a substrate is etched with etching gas having a high etching performance such as gas containing ozone, a uniform etching process can be performed.

DESCRIPTION OF EMBODIMENTS

Hereinafter, an embodiment of the present invention will be described. In the present embodiment, an etching apparatus including a vapor-phase deposition (VPD) chamber used in a VPD method will be described as an example.

Figure 1:
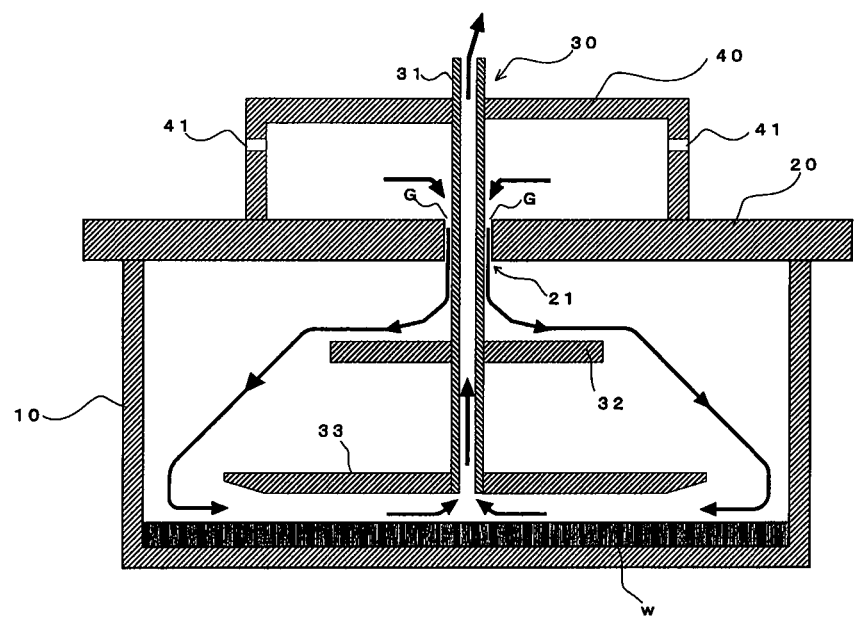
FIG. 1 is a schematic sectional view of an etching apparatus according to the present embodiment.

An etching apparatus of FIG. 1 includes a cylindrical chamber 10, a lid 20 arranged on an upper portion of the chamber 10, a gas supply means 30, and a buffer chamber 40 provided on an upper portion of the lid 20. A semiconductor substrate W serving as an etching target is arranged on a bottom portion of the chamber 10. Note that, although not illustrated, a carbon plate coated with polytetrafluoroethylene (PFA) is arranged as a temperature control means for a semiconductor substrate on the chamber bottom portion on which the semiconductor substrate W is arranged. It is possible to circulate temperature control water on the back side (the side opposite to the side on which the semiconductor substrate W is arranged) of the carbon plate.

Figure 2:
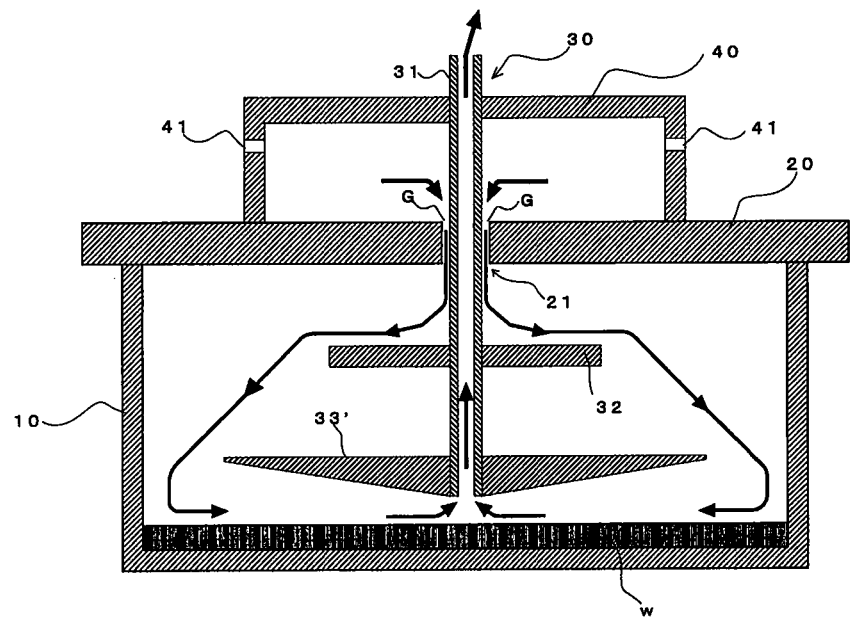
FIG. 2 is a schematic sectional view of an etching apparatus illustrating a gas-flow adjusting means.

A through hole 21 is provided at the center of the lid 20. An exhaust pipe 31 is provided as the gas supply means 30, and two disks 32 and 33 are attached to this exhaust pipe 31 as a gas-flow adjusting means. The disks 32 and 33 are installed to be movable vertically along the exhaust pipe. The gas-flow adjusting means may be a substantially conical member 33' having an apex on a substrate side, instead of the disk 33 (FIG. 2).

The disk 33 is processed such that a thickness of a cross-sectional shape of an outer circumferential portion decreases as it gets closer to an outer circumferential end. Specifically, in the present embodiment, the disk 33 has a shape having a notch portion on the lower side (the side facing the substrate) of the outer circumference of the disk 33 (FIG. 1). In addition, the diameter of the disk 32 is smaller than the diameter of the disk 33. Note that the number of disks can be arbitrarily changed and may be one or three or more.

An outer circumferential diameter of the exhaust pipe 31 is smaller than an inner diameter of the through hole 21 of the lid 20. The exhaust pipe 31 is installed in the through hole 21 of the lid 20 and arranged so as to have substantially the same center as the through hole 21. Accordingly, a gas introduction port G through which etching gas is introduced into the chamber 10 from the buffer chamber 40 is formed between the inner circumference of the through hole 21 and the outer circumference of the exhaust pipe 31

Four gas inlets 41 are installed in the buffer chamber 40 provided on the upper portion of the lid 20. Supplying etching gas into the buffer chamber 40 through the four gas inlets 41 and filling the buffer chamber sufficiently with the etching gas make it possible to introduce the etching gas having uniform composition and concentration into the chamber 10 through the gas introduction port G.

Analysis (an etching process) of a substrate using the above-described etching apparatus will be described. First, the semiconductor substrate W serving as the etching target is arranged on the bottom portion of the chamber 10. The lid 20 having the gas supply means 30 and the buffer chamber 40 is attached to the upper portion of the chamber 10, and the inside of the chamber is closed.

Next, the leading end of the exhaust pipe 31 is positioned above near the center of the semiconductor substrate W. The disks 32 and 33 attached to the exhaust pipe 31 are adjusted to appropriate height positions. Then, the etching gas is supplied through the four gas inlets 41 of the buffer chamber 40. The etching gas supplied through the four gas inlets 41 fills the inside of the buffer chamber 40 while being mixed and achieves uniform composition and concentration. The etching gas of the buffer chamber passes through the gas introduction port G and is introduced into the chamber 10.

In FIG. 1, thick arrows indicates the flow state of the etching gas introduced into the chamber 10. The disk 32 having a smaller diameter blocks the flow direction of the etching gas introduced into the chamber 10 and the etching gas flows in the outer circumferential direction of the disk 32. Then, the etching gas having flowed in the outer circumferential direction of the disk 32 having a smaller diameter flows in the outer circumferential direction of the semiconductor substrate W, that is, the periphery of the semiconductor substrate W by the disk 33 having a larger diameter arranged below the disk 32. The etching gas having flowed near the periphery of the semiconductor substrate W contacts the surface of the semiconductor substrate W, and an etching reaction occurs. Since the leading end of the exhaust pipe is positioned above the center of the semiconductor substrate W and the etching gas is exhausted through the exhaust pipe 31, the etching gas in the periphery of the semiconductor substrate W flows in the center direction of the semiconductor substrate W. Then, the etching gas contacts the entire surface of the semiconductor substrate W, and etching of the entire surface of the semiconductor substrate W is performed.

Figure 3:
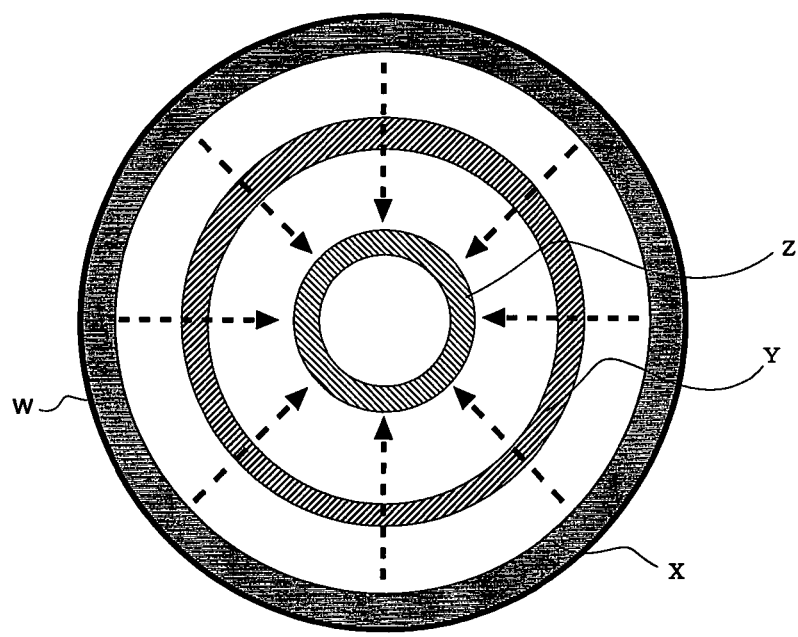
FIG. 3 is a schematic plan view illustrating an etching state of a semiconductor substrate surface.

FIG. 3 is a schematic plan view illustrating the flow direction of the etching gas and the etching state on the surface of the semiconductor substrate W. FIG. 3 is a view of the surface of the semiconductor substrate W viewed from the top, and schematically illustrates the flow of the etching gas flowing from the periphery of the semiconductor substrate W to the center of the semiconductor substrate by dotted line arrows. This flow of the etching gas occurs throughout the entire circumference of the semiconductor substrate W, and the dotted line arrows of FIG. 3 partially represent the flow of the etching gas.

The etching state of the semiconductor substrate will be described with reference to FIG. 3. Etching with the etching gas having flowed from the periphery of the semiconductor substrate W progresses sequentially for each region of a band-like circular portion X, a band-like circular portion Y, and a band-like circular portion Z in the substrate direction. First, the region of the band-like circular portion X is etched with the etching gas introduced into the periphery of the semiconductor substrate W. Next, the region of the band-like circular portion Y is etched with the etching gas passing through the band-like circular portion X, flowing toward the center and flowing to the band-like circular portion Y. The etching gas with which the band-like circular portion Y is etched has the component consumed to some extent due to etching of the peripheral side. However, since the band-like circular portion Y has a smaller area than the peripheral portion such as the band-like circular portion X, although the etching performance lowers slightly, the band-like circular portion Y has the same etching process result as the region such as the band-like circular portion X. Further, the etching gas passes through the band-like circular portion Y, and flows to the band-like circular portion Z near the center of the semiconductor substrate W. The etching gas in this band-like circular portion Z has the component further consumed, and a lower etching performance. However, since the area of the band-like circular portion Z is much smaller than the etching area of the further peripheral portion, the same etching process result as the regions of the band-like circular portion X and the band-like circular portion Y is obtained.

As described above, when the semiconductor substrate is etched by using the etching apparatus of FIG. 1, the component of the etching gas decreases and also the etching area decreases, and thus the same etching process result is obtained on all the regions. Thus, the uniform etching process can be realized on the entire surface of the semiconductor substrate. Note that, in FIG. 3, the etching region is divided into three, but actual etching is continuously performed from the periphery to the center of the semiconductor substrate.

Next, a result of performing the etching process by using the etching apparatus of FIG. 1 will be described. A silicon wafer base material having a diameter of 300 mm was used as the semiconductor substrate W serving as the etching target. This wafer base material has an oxide film or the like of the surface etched in advance, and the exposed bulk silicon. The etching process was performed on the substrate by using the etching apparatus illustrated in FIG. 1.

As etching gas, a hydrogen fluoride solution having a hydrogen fluoride concentration of 49 wt % was used, and vapor of hydrogen fluoride generated by atomizing the hydrogen fluoride solution was used. This gas was supplied to the buffer chamber 40 through the four gas inlets 41. In addition, at the same time, oxygen gas was supplied to a gas discharger (not illustrated), gas discharging was performed at an output 200 W to generate ozone-containing gas, and the ozone-containing gas was supplied to the buffer chamber 40 through the four gas inlets 41. In the buffer chamber 40, the vapor of the hydrogen fluoride is mixed with the ozone-containing gas to produce etching gas having uniform composition and concentration. This gas was introduced into the chamber 10 at a flow rate of 2 L/min through the gas introduction port G.

The exhaust pipe 31 and the two disks 32 and 33 configuring the gas supply means 30 of the etching apparatus were formed of a material of polytetrafluoroethylene (PTFE), the exhaust pipe 31 having the outer diameter of 12.7 mm and the inner diameter of 4 mm, the disk 32 having a smaller diameter with a diameter of 100 mm, and the disk 33 having a larger diameter with a diameter of 200 mm. Note that as a material constituting the gas supply means, in addition to the PTFE, polycarbonate, polyvinylidene fluoride, or the like can be used.

The exhaust pipe 31 was arranged to be vertically movable and was arranged such that the leading end of the exhaust pipe was positioned 15 mm above the surface of the wafer base material W. At this time, the disk 33 having a larger diameter was also arranged such that the lower surface of the disk was positioned 15 mm above the surface of the wafer base material W, and the disk 32 having a smaller diameter was arranged such that the lower surface of the disk was positioned 30 mm above the surface of the wafer base material W. Then, the used etching gas in the chamber 10 was forcibly exhausted through the exhaust pipe 31 at 2 L/min.

A substrate temperature was adjusted to 20° C., the etching process was performed for one hour, and bulk silicon was etched by 1.5 μm and removed. As an evaluation method, a wafer thickness before and after etching was measured by a commercially available semiconductor substrate thickness measuring apparatus. This thickness measurement was performed at 50,000 points on the wafer base material. As a result, it was found that the etching depth was 1.5±0.1 μm in 95% or more of the points.

As comparison, the etching was performed with the goal of the etching depth of 1.5 μm by the etching process of the conventional method (the case of using the etching processing apparatus disclosed in Patent Document 2) under the same etching condition (the condition in which the same wafer base material and the same etching gas were used). As a result, the etching depth by the conventional method was about 1.5±0.5 μm. In addition, there were points having a maximum etching depth of 3.0 μm and a minimum etching depth of 0.9 μm. In this way, a variation in the etching depth was observed in the etching by the conventional method.

Next, a result of examining the relationship between a substrate temperature and an etching speed will be described. Table 1 shows a result of performing the etching process for one hour while changing the substrate temperature in the above-described etching condition.

TABLE 1

| Substrate temperature | Average etching depth |
|---|---|
| 15° C. | 1.27 μm |
| 20° C. | 1.50 μm |
| 30° C. | 1.00 μm |
| 50° C. | 0.70 μm |

Table 1 shows that when the substrate temperature is 15° C., the etching speed is fast to some extent. On the other hand, however, when the substrate temperature was 15° C., the vapor of the etching gas was condensed, and a lot of etching unevenness was confirmed. On the other hand, when the substrate temperature became 30° C. or more, the etching speed was apparently slower than when the substrate temperature was 20° C. From this result, it was found that 20° C. is an optimal substrate temperature when the etching gas formed of the vapor of the hydrogen fluoride mixed with the ozone-containing gas is used as in the present embodiment.

INDUSTRIAL APPLICABILITY

According to the present invention, it is possible to uniformly etch polysilicon or bulk silicon which is relatively difficult to be decomposed even in the thickness direction of the substrate, and also it becomes possible to perform uniform etching of a large-area substrate in the surface direction. For this reason, efficient and highly accurate evaluation of semiconductor substrate characteristics and the like becomes possible.

REFERENCE SIGNS LIST

10 Chamber
20 Lid
21 Through hole
30 Gas supply means
31 Exhaust pipe
32, 33, 33' Gas-flow adjusting means
Buffer chamber
W Semiconductor substrate
G Gas introduction port

The invention claimed is:
1. An etching apparatus comprising a substantially cylindrical chamber having an upper portion, a bottom portion, and outer circumferential sides, in which a stationary substrate is arranged on the bottom portion, the etching apparatus comprising:
gas supply means for supplying etching gas to a substrate surface;
gas exhaust means for exhausting etched gas above substantially a center of the substrate; and
gas-flow adjusting means arranged on a substantially concentric circle above the substrate and allowing the etching gas to flow from a periphery of the substrate to substantially the center of the substrate, wherein the gas-flow adjusting means is installed in a vertically movable manner, and substantially a center of the gas-flow adjusting means is connected with the gas exhaust means; and wherein no inlets are present in the sides of the chamber.

2. The etching apparatus according to claim 1, wherein the gas-flow adjusting means has a disk shape or a substantially conical shape having an apex on a substrate side.

3. The etching apparatus according to claim 2, wherein the gas-flow adjusting means has a disk shape and is processed such that a thickness near an outer circumference decreases as the means gets closer to an outer circumferential end side.

4. The etching apparatus according to claim 3 wherein the upper portion of the chamber is closed by a lid, an exhaust pipe serving as the gas exhaust means is inserted into a through hole formed at a center of the lid, a leading end of the exhaust pipe is arranged above substantially the center of the substrate, a gas introduction section is positioned between an inner circumference of the through hole of the lid and an outer circumference of the exhaust pipe, and introduces the etching gas into the chamber, and the etching gas is introduced through the gas.

5. The etching apparatus according to claim 4 comprising, a buffer chamber that renders the etching gas to be supplied to the substrate surface uniform.

6. A method of analyzing a stationary substrate by using the etching apparatus, the etching apparatus defined in claim 4 comprising: etching polysilicon on the substrate or bulk silicon of the substrate with ozone-containing etching gas.

7. The etching apparatus according to claim 3 comprising, a buffer chamber that renders the etching gas to be supplied to the substrate surface uniform.

8. A method of analyzing a stationary substrate by using the etching apparatus, the etching apparatus defined in claim 3 comprising: etching polysilicon on the substrate or bulk silicon of the substrate with ozone-containing etching gas.

9. The etching apparatus according to claim 2 wherein the upper portion of the chamber is closed by a lid, an exhaust pipe serving as the gas exhaust means is inserted into a through hole formed at a center of the lid, a leading end of the exhaust pipe is arranged above substantially the center of the substrate, a gas introduction section is positioned between an inner circumference of the through hole of the lid and an outer circumference of the exhaust pipe, and introduces the etching gas into the chamber, and the etching gas is introduced through the gas.

10. The etching apparatus according to claim 9 comprising, a buffer chamber that renders the etching gas to be supplied to the substrate surface uniform.

11. A method of analyzing a stationary substrate by using the etching apparatus, the etching apparatus defined in claim 9 comprising: etching polysilicon on the substrate or bulk silicon of the substrate with ozone-containing etching gas.

12. The etching apparatus according to claim 2 comprising, a buffer chamber that renders the etching gas to be supplied to the substrate surface uniform.

13. A method of analyzing a stationary substrate by using the etching apparatus, the etching apparatus defined in claim 2 comprising: etching polysilicon on the substrate or bulk silicon of the substrate with ozone-containing etching gas.

14. The etching apparatus according to claim 1 wherein the upper portion of the chamber is closed by a lid, an exhaust pipe serving as the gas exhaust means is inserted into a through hole formed at a center of the lid, a leading end of the exhaust pipe is arranged above substantially the center of the substrate, a gas introduction section is positioned between an inner circumference of the through hole of the lid and an outer circumference of the exhaust pipe, and introduces the etching gas into the chamber, and the etching gas is introduced through the gas introduction section, flows from the outer circumference of the gas-flow adjusting means to the substrate surface, and can be exhausted from the leading end of the exhaust pipe.

15. The etching apparatus according to claim 14 comprising, a buffer chamber that renders the etching gas to be supplied to the substrate surface uniform.

16. A method of analyzing a stationary substrate by using the etching apparatus, the etching apparatus defined in claim 14 comprising: etching polysilicon on the substrate or bulk silicon of the substrate with ozone-containing etching gas.

17. The etching apparatus according to claim 1 comprising, a buffer chamber that renders the etching gas to be supplied to the substrate surface uniform.

18. A method of analyzing a stationary substrate by using the etching apparatus, the etching apparatus defined in claim 17 comprising: etching polysilicon on the substrate or bulk silicon of the substrate with ozone-containing etching gas.

19. A method of analyzing a stationary substrate by using the etching apparatus, the etching apparatus defined in claim 1 comprising: etching polysilicon on the substrate or bulk silicon of the substrate with ozone-containing etching gas.

20. The substrate analysis method according to claim 19, wherein a ratio (H/D) of a distance (H) between a substrate surface and a lowest end of a gas-flow adjusting means to a diameter (D) of the substrate is 1/60 to 1/10.

* * * * *